United States Patent
Nakamura et al.

(10) Patent No.: US 8,278,270 B2
(45) Date of Patent: *Oct. 2, 2012

(54) HGF PRECURSOR PROTEIN VARIANT AND ACTIVE PROTEIN THEREOF

(75) Inventors: Toshikazu Nakamura, Suita (JP); Kunio Matsumoto, Ibaraki (JP); Kazuhiro Fukuta, Minoh (JP); Kiichi Adachi, Toyonaka (JP); Daichika Hayata, Toyonaka (JP)

(73) Assignees: Kringle Pharma Inc., Osaka (JP); Osaka University, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/175,110

(22) Filed: Jul. 1, 2011

(65) Prior Publication Data

US 2011/0269944 A1 Nov. 3, 2011

Related U.S. Application Data

(62) Division of application No. 12/226,448, filed as application No. PCT/JP2007/057109 on Mar. 30, 2007, now Pat. No. 8,003,607.

(30) Foreign Application Priority Data

Apr. 20, 2006 (JP) ................................. 2006-116498

(51) Int. Cl.
A61K 38/18 (2006.01)
C12P 21/04 (2006.01)
C12P 21/06 (2006.01)
C12N 15/00 (2006.01)
C12N 5/00 (2006.01)
C07K 14/475 (2006.01)

(52) U.S. Cl. .... 514/9.5; 435/69.1; 435/70.1; 435/320.1; 435/325; 530/350; 530/399; 530/402; 530/407

(58) Field of Classification Search ........................ None
See application file for complete search history.

(56) References Cited

U.S. PATENT DOCUMENTS

| 5,879,910 | A | 3/1999 | Godowski et al. |
| 7,098,002 | B1 | 8/2006 | Rubinstein et al. |
| 7,220,569 | B2 | 5/2007 | Himmelspach et al. |
| 7,351,540 | B1 | 4/2008 | Carr |
| 2003/0124653 | A1 | 7/2003 | Canfield |
| 2004/0138120 | A1 | 7/2004 | Kirchhofer et al. |

OTHER PUBLICATIONS

T. Nakamura, "Kansaibo Zoshoku Inshi (HGF) no Bunshi Cloning", Experimental Medicine, 1990, vol. 8, No. 3, pp. 250-255 with an English translation thereof.
S. M. Hunt et al.,"Processing of mutated human proinsulin to mature insulin in the non-endocrine cell line, CHO", Cytotechnology, vol. 21, No. 3, pp. 279-288, 1996.
Peek, Mark et al., "Unusual Proteolytic Activation of Pro-hepatocyte Growth Factor by Plasma Kallikrein and Coagulation Factor XIa," Journal of Biological Chemistry, vol. 277, No. 49, pp. 47804-47809, 2002.

*Primary Examiner* — Marianne P Allen
(74) *Attorney, Agent, or Firm* — Wenderoth, Lind & Ponack, L.L.P.

(57) ABSTRACT

An HGF precursor protein variant, in which a peptide structure comprises a sequence including a peptide chain X inserted between an α chain of HGF or a polypeptide where 1 to 20 amino-acid residues from the C-terminus of the α chain are deleted, and a β chain of HGF or a polypeptide where 1 to 20 amino-acid residues from the N-terminus of the β chain are deleted; wherein (i) the peptide chain X has an amino-acid sequence of at least two residues, (ii) the peptide chain X can be cleaved by a protease reaction or a chemical reaction, and (iii) a protein obtained by cleaving at least one site of the peptide chain X has HGF action.

17 Claims, 2 Drawing Sheets

SEQUENCE LISTING

```
<160> NUMBER OF SEQ ID NOS: 21

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110
```

-continued

```
Gly His Glu Phe Asp Leu Tyr Glu Asn Lys Asp Tyr Ile Arg Asn Cys
            115                 120                 125
Ile Ile Gly Lys Gly Arg Ser Tyr Lys Gly Thr Val Ser Ile Thr Lys
    130                 135                 140
Ser Gly Ile Lys Cys Gln Pro Trp Ser Ser Met Ile Pro His Glu His
145                 150                 155                 160
Ser Phe Leu Pro Ser Ser Tyr Arg Gly Lys Asp Leu Gln Glu Asn Tyr
                165                 170                 175
Cys Arg Asn Pro Arg Gly Glu Glu Gly Gly Pro Trp Cys Phe Thr Ser
            180                 185                 190
Asn Pro Glu Val Arg Tyr Glu Val Cys Asp Ile Pro Gln Cys Ser Glu
        195                 200                 205
Val Glu Cys Met Thr Cys Asn Gly Glu Ser Tyr Arg Gly Leu Met Asp
    210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
            260                 265                 270
Thr Leu Asp Pro His Thr Arg Trp Glu Tyr Cys Ala Ile Lys Thr Cys
        275                 280                 285
Ala Asp Asn Thr Met Asn Asp Thr Asp Val Pro Leu Glu Thr Thr Glu
    290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
            340                 345                 350
Tyr Cys Arg Asn Pro Asp Gly Ser Glu Ser Pro Trp Cys Phe Thr Thr
        355                 360                 365
Asp Pro Asn Ile Arg Val Gly Tyr Cys Ser Gln Ile Pro Asn Cys Asp
    370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Asp Ala His
        435                 440                 445
Gly Pro Trp Cys Tyr Thr Gly Asn Pro Leu Ile Pro Trp Asp Tyr Cys
    450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
        515                 520                 525
Val Leu Thr Ala Arg Gln Cys Phe Pro Ser Arg Asp Leu Lys Asp Tyr
```

|     |     |     |     |     | 530 |     |     |     |     | 535 |     |     |     |     | 540 |     |

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
                595                 600                 605

Lys Thr Ser Cys Ser Val Tyr Gly Trp Gly Tyr Thr Gly Leu Ile Asn
                610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
                675                 680                 685

Gly Val Ile Val Pro Gly Arg Gly Cys Ala Ile Pro Asn Arg Pro Gly
                690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 2
<211> LENGTH: 723
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Ser Ala Lys Thr
                35                  40                  45

Thr Leu Ile Lys Ile Asp Pro Ala Leu Lys Ile Lys Thr Lys Val
50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
                115                 120                 125

Ile Ile Gly Lys Gly Arg Ser Tyr Lys Gly Thr Val Ser Ile Thr Lys
                130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg

-continued

```
                180                 185                 190
Tyr Glu Val Cys Asp Ile Pro Gln Cys Ser Glu Val Glu Cys Met Thr
                195                 200                 205
Cys Asn Gly Glu Ser Tyr Arg Gly Leu Met Asp His Thr Glu Ser Gly
    210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
            260                 265                 270
Thr Arg Trp Glu Tyr Cys Ala Ile Lys Thr Cys Ala Asp Asn Thr Met
        275                 280                 285
Asn Asp Thr Asp Val Pro Leu Glu Thr Thr Glu Cys Ile Gln Gly Gln
    290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
        355                 360                 365
Val Gly Tyr Cys Ser Gln Ile Pro Asn Cys Asp Met Ser His Gly Gln
    370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
            420                 425                 430
Asn Tyr Cys Arg Asn Pro Asp Asp Asp Ala His Gly Pro Trp Cys Tyr
        435                 440                 445
Thr Gly Asn Pro Leu Ile Pro Trp Asp Tyr Cys Pro Ile Ser Arg Cys
    450                 455                 460
Glu Gly Asp Thr Thr Pro Thr Ile Val Asn Leu Asp His Pro Val Ile
465                 470                 475                 480
Ser Cys Ala Lys Thr Lys Gln Leu Arg Val Val Asn Gly Ile Pro Thr
                485                 490                 495
Arg Thr Asn Ile Gly Trp Met Val Ser Leu Arg Tyr Arg Asn Lys His
            500                 505                 510
Ile Cys Gly Gly Ser Leu Ile Lys Glu Ser Trp Val Leu Thr Ala Arg
        515                 520                 525
Gln Cys Phe Pro Ser Arg Asp Leu Lys Asp Tyr Glu Ala Trp Leu Gly
    530                 535                 540
Ile His Asp Val His Gly Arg Gly Asp Glu Lys Cys Lys Gln Val Leu
545                 550                 555                 560
Asn Val Ser Gln Leu Val Tyr Gly Pro Glu Gly Ser Asp Leu Val Leu
                565                 570                 575
Met Lys Leu Ala Arg Pro Ala Val Leu Asp Asp Phe Val Ser Thr Ile
            580                 585                 590
Asp Leu Pro Asn Tyr Gly Cys Thr Ile Pro Glu Lys Thr Ser Cys Ser
        595                 600                 605
```

```
Val Tyr Gly Trp Gly Tyr Thr Gly Leu Ile Asn Tyr Asp Gly Leu Leu
            610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                    645                 650                 655

Glu Lys Ile Gly Ser Gly Pro Cys Glu Gly Asp Tyr Gly Gly Pro Leu
                660                 665                 670

Val Cys Glu Gln His Lys Met Arg Met Val Leu Gly Val Ile Val Pro
            675                 680                 685

Gly Arg Gly Cys Ala Ile Pro Asn Arg Pro Gly Ile Phe Val Arg Val
        690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Asp Asp Asp Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct

<400> SEQUENCE: 4

Ile Glu Gly Arg
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct

<400> SEQUENCE: 5

Ile Asp Gly Arg
1

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct

<400> SEQUENCE: 6

Leu Val Pro Arg Gly Ser
1               5

<210> SEQ ID NO 7
<211> LENGTH: 7
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any amino-acid residue

<400> SEQUENCE: 7

Glu Xaa Xaa Tyr Phe Gln Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any amino-acid residue

<400> SEQUENCE: 8

Glu Xaa Xaa Tyr Phe Gln Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Leu Glu Val Leu Phe Gln Gly Pro
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any amino-acid residue

<400> SEQUENCE: 10

Arg Xaa Lys Arg
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any amino-acid residue

<400> SEQUENCE: 11

Arg Xaa Arg Arg
1

<210> SEQ ID NO 12
<211> LENGTH: 6
<212> TYPE: PRT
```

```
<213> ORGANISM: Artificial Sequence
<220> FEATURE:
<223> OTHER INFORMATION: Synthetic Construct

<400> SEQUENCE: 12

Pro Gly Ala Ala His Tyr
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

Pro Gly Ala Ala Tyr His
1               5

<210> SEQ ID NO 14
<211> LENGTH: 723
<212> TYPE: PRT
<213> ORGANISM: Artificial Sequence
<220> FEATURE:
<223> OTHER INFORMATION: Synthetic Construct

<400> SEQUENCE: 14

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255
```

-continued

```
Asn Pro Asp Gly Gln Pro Arg Pro Trp Cys Tyr Thr Leu Asp Pro His
            260             265             270
Thr Arg Trp Glu Tyr Cys Ala Ile Lys Thr Cys Ala Asp Asn Thr Met
        275             280             285
Gln Asp Thr Asp Val Pro Leu Glu Thr Thr Glu Cys Ile Gln Gly Gln
290             295             300
Gly Glu Gly Tyr Arg Gly Thr Val Asn Thr Ile Trp Asn Gly Ile Pro
305             310             315             320
Cys Gln Arg Trp Asp Ser Gln Tyr Pro His Glu His Asp Met Thr Pro
                325             330             335
Glu Asn Phe Lys Cys Lys Asp Leu Arg Glu Asn Tyr Cys Arg Asn Pro
            340             345             350
Asp Gly Ser Glu Ser Pro Trp Cys Phe Thr Thr Asp Pro Asn Ile Arg
        355             360             365
Val Gly Tyr Cys Ser Gln Ile Pro Asn Cys Asp Met Ser His Gly Gln
    370             375             380
Asp Cys Tyr Arg Gly Asn Gly Lys Asn Tyr Met Gly Gln Leu Ser Gln
385             390             395             400
Thr Arg Ser Gly Leu Thr Cys Ser Met Trp Asp Lys Asn Met Glu Asp
                405             410             415
Leu His Arg His Ile Phe Trp Glu Pro Asp Ala Ser Lys Leu Asn Glu
            420             425             430
Asn Tyr Cys Arg Asn Pro Asp Asp Ala His Gly Pro Trp Cys Tyr
        435             440             445
Thr Gly Asn Pro Leu Ile Pro Trp Asp Tyr Cys Pro Ile Ser Arg Cys
    450             455             460
Glu Gly Asp Thr Thr Pro Gly Ile Val Asn Leu Asp His Pro Val Ile
465             470             475             480
Ser Cys Ala Lys Thr Lys Gln Leu Arg Val Val Asn Gly Ile Pro Thr
                485             490             495
Arg Thr Asn Ile Gly Trp Met Val Ser Leu Arg Tyr Arg Asn Lys His
            500             505             510
Ile Cys Gly Gly Ser Leu Ile Lys Glu Ser Trp Val Leu Thr Ala Arg
        515             520             525
Gln Cys Phe Pro Ser Arg Asp Leu Lys Asp Tyr Glu Ala Trp Leu Gly
    530             535             540
Ile His Asp Val His Gly Arg Gly Asp Glu Lys Cys Lys Gln Val Leu
545             550             555             560
Gln Val Ser Gln Leu Val Tyr Gly Pro Glu Gly Ser Asp Leu Val Leu
                565             570             575
Met Lys Leu Ala Arg Pro Ala Val Leu Asp Asp Phe Val Ser Thr Ile
            580             585             590
Asp Leu Pro Asn Tyr Gly Cys Thr Ile Pro Glu Lys Thr Ser Cys Ser
        595             600             605
Val Tyr Gly Trp Gly Tyr Thr Gly Leu Ile Asn Tyr Asp Gly Leu Leu
    610             615             620
Arg Val Ala His Leu Tyr Ile Met Gly Asn Glu Lys Cys Ser Gln His
625             630             635             640
His Arg Gly Lys Val Thr Leu Gln Glu Ser Glu Ile Cys Ala Gly Ala
                645             650             655
Glu Lys Ile Gly Ser Gly Pro Cys Glu Gly Asp Tyr Gly Gly Pro Leu
            660             665             670
Val Cys Glu Gln His Lys Met Arg Met Val Leu Gly Val Ile Val Pro
        675             680             685
```

```
Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 15
<211> LENGTH: 2172
<212> TYPE: DNA
<213> ORGANISM: Homo sapiens

<400> SEQUENCE: 15
```

| | | | | | |
|---|---|---|---|---|---|
| atgtgggtga | ccaaactcct | gccagccctg | ctgctgcagc | atgtcctcct | gcatctcctc | 60 |
| ctgctcccca | tcgccatccc | ctatgcagag | ggacaaagga | aaagaagaaa | tacaattcat | 120 |
| gaattcaaaa | aatcagcaaa | gactacccta | atcaaaatag | atccagcact | gaagataaaa | 180 |
| accaaaaaag | tgaatactgc | agaccaatgt | gctaatagat | gtactaggaa | taaaggactt | 240 |
| ccattcactt | gcaaggcttt | tgttttgat | aaagcaagaa | acaatgcct | ctggttcccc | 300 |
| ttcaatagca | tgtcaagtgg | agtgaaaaaa | gaatttggcc | atgaatttga | cctctatgaa | 360 |
| aacaaagact | acattagaaa | ctgcatcatt | ggtaaaggac | gcagctacaa | gggaacagta | 420 |
| tctatcacta | gagtggcat | caaatgtcag | ccctggagtt | ccatgatacc | acacgaacac | 480 |
| agctatcggg | gtaaagacct | acaggaaaac | tactgtcgaa | atcctcgagg | ggaagaaggg | 540 |
| ggaccctggt | gtttcacaag | caatccagag | gtacgctacg | aagtctgtga | cattcctcag | 600 |
| tgttcagaag | ttgaatgcat | gacctgcaat | ggggagagtt | atcgaggtct | catggatcat | 660 |
| acagaatcag | gcaagatttg | tcagcgctgg | gatcatcaga | caccacaccg | gcacaaattc | 720 |
| ttgcctgaaa | gatatcccga | caagggcttt | gatgataatt | attgccgcaa | tcccgatggc | 780 |
| cagccgaggc | catggtgcta | tactcttgac | cctcacaccc | gctgggagta | ctgtgcaatt | 840 |
| aaaacatgcg | ctgacaatac | tatgcaagac | actgatgttc | ctttggaaac | aactgaatgc | 900 |
| atccaaggtc | aaggagaagg | ctacaggggc | actgtcaata | ccatttggaa | tggaattcca | 960 |
| tgtcagcgtt | gggattctca | gtatcctcac | gagcatgaca | tgactcctga | aaatttcaag | 1020 |
| tgcaaggacc | tacgagaaaa | ttactgccga | aatccagatg | gtctgaatc | accctggtgt | 1080 |
| tttaccactg | atccaaacat | ccgagttggc | tactgctccc | aaattccaaa | ctgtgatatg | 1140 |
| tcacatggac | aagattgtta | tcgtgggaat | ggcaaaaatt | atatgggcca | gttatcccaa | 1200 |
| acaagatctg | gactaacatg | ttcaatgtgg | gacaagaaca | tggaagactt | acatcgtcat | 1260 |
| atcttctggg | aaccagatgc | aagtaagctg | aatgagaatt | actgccgaaa | tccagatgat | 1320 |
| gatgctcatg | gaccctggtg | ctacacggga | aatccactca | ttccttggga | ttattgccct | 1380 |
| atttctcgtt | gtgaaggtga | taccacacct | ggaatagtca | atttagacca | tcccgtaata | 1440 |
| tcttgtgcca | aaacgaaaca | attgcgagtt | gtaaatggga | ttccaacacg | aacaaacata | 1500 |
| ggatggatgg | ttagtttgag | atacagaaat | aaacatatct | gcggaggatc | attgataaag | 1560 |
| gagagttggg | ttcttactgc | acgacagtgt | ttcccttctc | gagacttgaa | agattatgaa | 1620 |
| gcttggcttg | gaattcatga | tgtccacgga | agaggagatg | agaaatgcaa | acaggttctc | 1680 |
| caagtttccc | agctggtata | tggccctgaa | ggatcagatc | tggttttaat | gaagcttgcc | 1740 |
| aggcctgctg | tcctggatga | ttttgttagt | acgattgatt | tacctaatta | tggatgcaca | 1800 |
| attcctgaaa | agaccagttg | cagtgtttat | ggctggggct | acactggatt | gatcaactat | 1860 |
| gatggcctat | tacgagtggc | acatctctat | ataatgggaa | atgagaaatg | cagccagcat | 1920 |

```
catcgaggga aggtgactct gcaagagtct gaaatatgtg ctggggctga aaagattgga    1980
tcaggaccat gtgaggggga ttatggtggc ccacttgttt gtgagcaaca taaaatgaga    2040
atggttcttg gtgtcattgt tcctggtcgt ggatgtgcca ttccaaatcg tcctggtatt    2100
tttgtccgag tagcatatta tgcaaaatgg atacacaaaa ttattttaac atataaggta    2160
ccacagtcat ag                                                        2172
```

<210> SEQ ID NO 16
<211> LENGTH: 43
<212> TYPE: DNA
<213> ORGANISM: Artificial Sequence
<220> FEATURE:
<223> OTHER INFORMATION: Synthetic Construct; primer

<400> SEQUENCE: 16

```
ccaaaacgaa acaacactat gttgtaaatg ggattccaac acg                       43
```

<210> SEQ ID NO 17
<211> LENGTH: 37
<212> TYPE: DNA
<213> ORGANISM: Artificial Sequence
<220> FEATURE:
<223> OTHER INFORMATION: Synthetic Construct; primer

<400> SEQUENCE: 17

```
cgaaacaatt gtatcacgta aatgggattc caacacg                              37
```

<210> SEQ ID NO 18
<211> LENGTH: 44
<212> TYPE: DNA
<213> ORGANISM: Artificial Sequence
<220> FEATURE:
<223> OTHER INFORMATION: Synthetic Construct; primer

<400> SEQUENCE: 18

```
gtaatatctt gtgccccagg ggccgcacac tatgttgtaa atgg                      44
```

<210> SEQ ID NO 19
<211> LENGTH: 723
<212> TYPE: PRT
<213> ORGANISM: Artificial Sequence
<220> FEATURE:
<223> OTHER INFORMATION: Synthetic Construct

<400> SEQUENCE: 19

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125
```

```
Ile Ile Gly Lys Gly Arg Ser Tyr Lys Gly Thr Val Ser Ile Thr Lys
    130                 135                 140
Ser Gly Ile Lys Cys Gln Pro Trp Ser Ser Met Ile Pro His Glu His
145                 150                 155                 160
Ser Tyr Arg Gly Lys Asp Leu Gln Glu Asn Tyr Cys Arg Asn Pro Arg
                165                 170                 175
Gly Glu Gly Gly Pro Trp Cys Phe Thr Ser Asn Pro Glu Val Arg
            180                 185                 190
Tyr Glu Val Cys Asp Ile Pro Gln Cys Ser Glu Val Glu Cys Met Thr
        195                 200                 205
Cys Asn Gly Glu Ser Tyr Arg Gly Leu Met Asp His Thr Glu Ser Gly
    210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
            260                 265                 270
Thr Arg Trp Glu Tyr Cys Ala Ile Lys Thr Cys Ala Asp Asn Thr Met
        275                 280                 285
Gln Asp Thr Asp Val Pro Leu Glu Thr Thr Glu Cys Ile Gln Gly Gln
    290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
        355                 360                 365
Val Gly Tyr Cys Ser Gln Ile Pro Asn Cys Asp Met Ser His Gly Gln
    370                 375                 380
Asp Cys Tyr Arg Gly Asn Gly Lys Asn Tyr Met Gly Gln Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
            420                 425                 430
Asn Tyr Cys Arg Asn Pro Asp Asp Asp Ala His Gly Pro Trp Cys Tyr
        435                 440                 445
Thr Gly Asn Pro Leu Ile Pro Trp Asp Tyr Cys Pro Ile Ser Arg Cys
    450                 455                 460
Glu Gly Asp Thr Thr Pro Gly Ile Val Asn Leu Asp His Pro Val Ile
465                 470                 475                 480
Ser Cys Ala Lys Thr Lys Gln His Tyr Val Val Asn Gly Ile Pro Thr
                485                 490                 495
Arg Thr Asn Ile Gly Trp Met Val Ser Leu Arg Tyr Arg Asn Lys His
            500                 505                 510
Ile Cys Gly Gly Ser Leu Ile Lys Glu Ser Trp Val Leu Thr Ala Arg
        515                 520                 525
Gln Cys Phe Pro Ser Arg Asp Leu Lys Asp Tyr Glu Ala Trp Leu Gly
    530                 535                 540
Ile His Asp Val His Gly Arg Gly Asp Glu Lys Cys Lys Gln Val Leu
```

```
                      545                 550                 555                 560

Gln Val Ser Gln Leu Val Tyr Gly Pro Glu Gly Ser Asp Leu Val Leu
                     565                 570                 575

Met Lys Leu Ala Arg Pro Ala Val Leu Asp Asp Phe Val Ser Thr Ile
                 580                 585                 590

Asp Leu Pro Asn Tyr Gly Cys Thr Ile Pro Glu Lys Thr Ser Cys Ser
                 595                 600                 605

Val Tyr Gly Trp Gly Tyr Thr Gly Leu Ile Asn Tyr Asp Gly Leu Leu
             610                 615                 620

Arg Val Ala His Leu Tyr Ile Met Gly Asn Glu Lys Cys Ser Gln His
     625                 630                 635                 640

His Arg Gly Lys Val Thr Leu Gln Glu Ser Glu Ile Cys Ala Gly Ala
                     645                 650                 655

Glu Lys Ile Gly Ser Gly Pro Cys Glu Gly Asp Tyr Gly Gly Pro Leu
                 660                 665                 670

Val Cys Glu Gln His Lys Met Arg Met Val Leu Gly Val Ile Val Pro
             675                 680                 685

Gly Arg Gly Cys Ala Ile Pro Asn Arg Pro Gly Ile Phe Val Arg Val
         690                 695                 700

Ala Tyr Tyr Ala Lys Trp Ile His Lys Ile Ile Leu Thr Tyr Lys Val
     705                 710                 715                 720

Pro Gln Ser

<210> SEQ ID NO 20
<211> LENGTH: 723
<212> TYPE: PRT
<213> ORGANISM: Artificial Sequence
<220> FEATURE:
<223> OTHER INFORMATION: Synthetic Construct

<400> SEQUENCE: 20

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190
```

```
Tyr Glu Val Cys Asp Ile Pro Gln Cys Ser Glu Val Glu Cys Met Thr
        195                 200                 205
Cys Asn Gly Glu Ser Tyr Arg Gly Leu Met Asp His Thr Glu Ser Gly
        210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
            260                 265                 270
Thr Arg Trp Glu Tyr Cys Ala Ile Lys Thr Cys Ala Asp Asn Thr Met
        275                 280                 285
Gln Asp Thr Asp Val Pro Leu Glu Thr Thr Glu Cys Ile Gln Gly Gln
        290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
        355                 360                 365
Val Gly Tyr Cys Ser Gln Ile Pro Asn Cys Asp Met Ser His Gly Gln
        370                 375                 380
Asp Cys Tyr Arg Gly Asn Gly Lys Asn Tyr Met Gly Gln Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
            420                 425                 430
Asn Tyr Cys Arg Asn Pro Asp Asp Asp Ala His Gly Pro Trp Cys Tyr
        435                 440                 445
Thr Gly Asn Pro Leu Ile Pro Trp Asp Tyr Cys Pro Ile Ser Arg Cys
        450                 455                 460
Glu Gly Asp Thr Thr Pro Gly Ile Val Asn Leu Asp His Pro Val Ile
465                 470                 475                 480
Ser Cys Ala Pro Gly Ala Ala His Tyr Val Val Asn Gly Ile Pro Thr
                485                 490                 495
Arg Thr Asn Ile Gly Trp Met Val Ser Leu Arg Tyr Arg Asn Lys His
            500                 505                 510
Ile Cys Gly Gly Ser Leu Ile Lys Glu Ser Trp Val Leu Thr Ala Arg
        515                 520                 525
Gln Cys Phe Pro Ser Arg Asp Leu Lys Asp Tyr Glu Ala Trp Leu Gly
        530                 535                 540
Ile His Asp Val His Gly Arg Gly Asp Glu Lys Cys Lys Gln Val Leu
545                 550                 555                 560
Gln Val Ser Gln Leu Val Tyr Gly Pro Glu Gly Ser Asp Leu Val Leu
                565                 570                 575
Met Lys Leu Ala Arg Pro Ala Val Leu Asp Asp Phe Val Ser Thr Ile
            580                 585                 590
Asp Leu Pro Asn Tyr Gly Cys Thr Ile Pro Glu Lys Thr Ser Cys Ser
        595                 600                 605
Val Tyr Gly Trp Gly Tyr Thr Gly Leu Ile Asn Tyr Asp Gly Leu Leu
        610                 615                 620
```

```
Arg Val Ala His Leu Tyr Ile Met Gly Asn Glu Lys Cys Ser Gln His
625                 630                 635                 640

His Arg Gly Lys Val Thr Leu Gln Glu Ser Glu Ile Cys Ala Gly Ala
                645                 650                 655

Glu Lys Ile Gly Ser Gly Pro Cys Glu Gly Asp Tyr Gly Gly Pro Leu
                660                 665                 670

Val Cys Glu Gln His Lys Met Arg Met Val Leu Gly Val Ile Val Pro
                675                 680                 685

Gly Arg Gly Cys Ala Ile Pro Asn Arg Pro Gly Ile Phe Val Arg Val
        690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 21
<211> LENGTH: 5
<212> TYPE: PRT
<213> ORGANISM: Artificial Sequence
<220> FEATURE:
<223> OTHER INFORMATION: Synthetic Construct

<400> SEQUENCE: 21

Val Val Asn Gly Ile
1               5
```

HGF PRECURSOR PROTEIN VARIANT AND ACTIVE PROTEIN THEREOF

This application is a divisional of Ser. No. 12/226,448, filed Jan. 30, 2009, which is now U.S. Pat. No. 8,003,607, which is a 371 U.S. national stage of International Application No. PCT/JP2007/057109, filed Mar. 30, 2007 herein incorporated by reference in its entirety.

TECHNICAL FIELD

The present invention relates to an HGF precursor protein variant that can be activated without serum. More specifically, the present invention relates to a single-stranded HGF precursor protein variant comprising a sequence including a peptide chain X, which has an amino-acid sequence composed of at least two residues that can be cleaved by a protease reaction or a chemical reaction, inserted between the α chain and the β chain of the HGF. The present invention also relates to an active HGF protein variant obtained from the variant by cleaving one site in the amino-acid sequence of the inserted peptide chain X. Further, the present invention relates to a method for producing an active HGF protein variant.

BACKGROUND ART

Hepatocyte growth factor (HGF) was found as a protein having hepatocyte proliferation action, and subsequent studies have shown that the HGF is a physiologically active protein having various kinds of pharmacological activities other than the proliferation action of hepatocytes. The pharmacological activities are described, for example, in Jikken Igaku zoukan 10(3) pp. 330-339 (1992).

Based on the diverse activities of HGF, other names of HGF including SF (scatter factor) and TCF (tumor cytotoxic factor) are used. However, in the present invention, these known proteins having proliferation action of hepatocytes are collectively referred to as HGF. Because of its pharmacological activities, expected is the development of HGF as a cirrhosis drug, a renal disease drug, an epithelial cell proliferation accelerant, an anticancer drug, an anti-side-effect drug for cancer therapy, a lung disorder drug, a gastroduodenal damage drug, a cranial nerve disorder drug, an immunosuppressive anti-side-effect drug, a collagen-degrading promoter, a cartilage disorder drug, an arterial disease drug, a pulmonary fibrosis drug, a liver disorder drug, a blood coagulation disorder drug, a hypoproteinemia drug, a wound healing drug, a neuropathy drug, a hematopoietic stem cell augmenter and hair growth promotion drug, etc. (see, for example, JP-A No. 4-18028, JP-A No. 4-49246, JP-A No. 7-179356, JP-A No. 6-25010, JP-A No. 6-340546, JP-A No. 6-172207, JP-A No. 7-89869, JP-A No. 6-40934, JP-A No. 6-503949, JP-A No. 6-40935, JP-A No. 6-56692, JP-A No. 7-41429, JP3395181 and JP-A No. 5-213721).

HGF is secreted from organs such as the liver, kidneys, lungs, brain, bone marrow, spleen, and placenta, or from blood cells such as platelets and leukocytes. However, as the in vivo content of HGF is infinitesimal, in order to use HGF as a medicinal preparation, a large amount of HGF should be produced by a genetic engineering technique using cells. It is conventionally known that HGF can be produced using animal cells such as Chinese hamster ovary (CHO) cells (see, for example, JP-A No. 11-4696 and JP-A No. 10-191991).

In cultivating animal cells, fetal bovine serum has conventionally been added. However, recently, serum-free cultivation has been advanced. Therefore, to produce a protein for use as a medicinal preparation with the use of animal cells such as CHO cells, cultivation is generally performed under a serum-free condition. This is because by not using fetal bovine serum, production costs can be reduced and the risk of contamination of viruses and abnormal prions derived from fetal bovine serum can be avoided. Even when HGF is produced using animal cells such as CHO cells, serum-free cultivation can be employed. In this case, however, there is a problem that HGF can be produced only as an inactive HGF precursor protein.

In the biosynthesis of HGF, single-stranded HGF precursor protein is first synthesized and secreted from cells. This HGF precursor protein is an inactive precursor. It is not until the HGF precursor protein is cleaved by the action of a protease called HGF activator (HGFA) and converted into a double stranded structure that the HGF becomes active. This activated HGF is a heterodimer comprising an α chain and a β chain. HGFA itself is also originally biosynthesized as an inactive single-stranded precursor (hereinafter also referred to as pro-HGFA), and is normally circulating in the form of pro-HGFA in the plasma. In the event of tissue injury, working with blood-clotting system and the like, the pro-HGFA is cleaved by the action of thrombin and becomes an active double-stranded HGFA to activate the HGF precursor protein. As serum is in a state where blood-clotting system has already worked, HGFA exists in its active form in serum. Therefore, when CHO cells into which DNA encoding HGF is introduced are cultivated in the presence of serum, HGF produced in culture medium is in its active form by the action of active HGFA in serum. Meanwhile, when the CHO cells are cultivated under a serum-free condition, because of the absence of HGFA, HGF is produced only as an inactive HGF precursor protein. Although it might be a possible option that HGFA, instead of serum, is added to the cultivation system of CHO cells, there is difficulty in obtaining an active HGFA in the absence of serum because of a cascade that, as described above, HGFA is also secreted as an inactive single-stranded pro-HGFA and then converted into an active HGFA in conjunction with blood-clotting system. Therefore, with conventional technique, an active HGF cannot be efficiently produced unless serum is added.

Consequently, development of a method to activate HGF precursor protein without adding serum has been desired. If such a method becomes available, an active HGF can be safely produced even when CHO cells are cultivated under a serum-free condition, and the risk of contamination of viruses and abnormal prions can be avoided. In addition, serum-free host systems in which yeast and an individual insect, etc. are used as hosts for recombinant production of HGF become available, and the method can be applied to a production system in which HGF expression at a higher level than in CHO cells can be expected.

However, such a method to activate HGF precursor protein without adding serum was previously unknown.

DISCLOSURE OF THE INVENTION

Problems to be Solved by the Invention

An object of the present invention is to provide an HGF precursor protein variant that can be converted without serum into an active HGF protein variant (an active heterodimer), an active HGF protein thereof and a preparation method thereof.

Means for Solving the Problems

To achieve the above-mentioned object, the present inventors have intensively carried out investigations on the activation of HGF precursor protein, and finally found that an HGF precursor protein variant comprising a peptide chain X, which has an amino-acid sequence of at least two residues that can be cleavage by a protease reaction or a chemical reaction, inserted between the α chain and the β chain thereof can be converted without serum into an active double-stranded HGF protein variant. Cleaving the sequence of the peptide chain X inserted between the α chain and the β chain using a protease or a chemical treatment agent capable of cleaving the cleavable sequence converts the HGF precursor protein variant into an active HGF protein variant, which is a disulfide (S—S)-bound heterodimer, showing the bioaction of HGF. Based on the above findings, the present inventors have carried out further investigations and completed the present invention.

That is, the present invention provides an HGF precursor protein variant that can be converted without serum into an active heterodimer, an active HGF protein thereof and a preparation method thereof. Further, the present invention provides a medicinal preparation comprising an active HGF protein variant as an active ingredient.

Namely, the present invention relates to:

(1) an HGF precursor protein variant, in which a peptide structure comprises a sequence including a peptide chain X inserted between an α chain of HGF or a polypeptide where 1 to 20 amino-acid residues from the C-terminus of the α chain are deleted, and a β chain of HGF or a polypeptide where 1 to 20 amino-acid residues from the N-terminus of the β chain are deleted; wherein (i) the peptide chain X has an amino-acid sequence of at least two residues, (ii) the peptide chain X can be cleaved by a protease reaction or a chemical reaction, and (iii) a protein obtained by cleaving at least one site of the peptide chain X has HGF action;

(2) the HGF precursor protein variant according to the above-mentioned (1), wherein the peptide chain X has a protease recognition sequence;

(3) the HGF precursor protein variant according to the above-mentioned (2), wherein the protease recognition sequence is at least one protease recognition sequence selected from the group consisting of Genenase I recognition sequence, Enterokinase recognition sequence, blood coagulation factor Xa recognition sequence, thrombin recognition sequence, TEV protease recognition sequence, Rhinovirus 3C protease recognition sequence and Furin recognition sequence;

(4) the HGF precursor protein variant according to the above-mentioned (2), wherein the protease recognition sequence is His-Tyr or Tyr-His;

(5) the HGF precursor protein variant according to any of the above-mentioned (1) to (4), wherein the HGF is of human, canine or feline origin;

(6) the HGF precursor protein variant according to any of the above-mentioned (1) to (4), wherein the HGF is of human origin;

(7) the HGF precursor protein variant according to the above-mentioned (6), wherein the HGF is (a) a protein comprising an amino-acid sequence represented by SEQ ID NO: 1 or SEQ ID NO: 2;

(b) a protein comprising an amino-acid sequence represented by SEQ ID NO: 1 or SEQ ID NO: 2 wherein one or several amino-acid residues are deleted, substituted or added, and having substantially the same action as that of HGF; or (c) a protein comprising an amino-acid sequence having a 80% homology or more with the amino-acid sequence represented by SEQ ID NO: 1 or SEQ ID NO: 2, and having substantially the same action as that of HGF;

(8) the HGF precursor protein variant according to the above-mentioned (6), wherein the α-chain is (a) an amino-acid sequence from the 32nd to the 494th of the sequence represented by SEQ ID NO: 1, and the β-chain is (b) an amino-acid sequence from the 495th to the 728th of the sequence represented by SEQ ID NO: 1; or alternatively the α-chain is (c) an amino-acid sequence from the 32nd to the 489th of the sequence represented by SEQ ID NO: 2, and the β-chain is (d) an amino-acid sequence from the 490th to the 723th of the sequence represented by SEQ ID NO: 2;

(9) an active HGF protein variant obtained by cleaving at least one site of the peptide chain X in the HGF precursor protein variant according to any of the above-mentioned (1) to (8);

(10) the active HGF protein variant according to the above-mentioned (9), wherein the cleavage is caused by a protease treatment or a chemical treatment;

(11) the active HGF protein variant according to the above-mentioned (10), wherein the protease is at least one protease selected from the group consisting of Genenase I, Enterokinase, blood coagulation factor Xa, thrombin, TEV protease, Rhinovirus 3C protease and Furin;

(12) the active HGF protein variant according to the above-mentioned (10), wherein the cleavage occurs at the C terminus of His-Tyr or Tyr-His;

(13) the active HGF protein variant according to the above-mentioned (10) or (12), wherein the cleavage is caused by Genenase I treatment;

(14) the active HGF protein variant according to the above-mentioned (9), wherein the cleavage is caused by a chemical cleavage method;

(15) a method for producing the active HGF protein variant, comprising producing the HGF precursor protein variant according to any of the above-mentioned (1) to (8), and simultaneously or subsequently converting the HGF precursor protein variant into an active HGF protein variant by cleaving at least one site of the peptide chain X;

(16) the method for producing the active HGF protein variant according to the above-mentioned (15), wherein the cleavage is caused by a protease treatment or a chemical treatment;

(17) the method for producing the active HGF protein variant according to the above-mentioned (16), wherein the protease is at least one protease selected from the group consisting of Genenase I, Enterokinase, blood coagulation factor Xa, thrombin, TEV protease, Rhinovirus 3C protease and Furin;

(18) the method for producing the active HGF protein variant according to the above-mentioned (15), comprising producing a single-stranded HGF precursor protein variant having a sequence into which a peptide chain X having a sequence of His-Tyr or Tyr-His and 2 to 20 amino acid residues, is inserted, and simultaneously or subsequently treating the HGF precursor protein variant with Genenase I;

(19) the method for producing the active HGF protein variant according to any of the above-mentioned (16) to (18), wherein a DNA coding for the HGF precursor protein variant according to any of the above-mentioned (1) to (8) and a DNA coding for a protease to cleave the peptide chain X are simultaneously introduced into a host, the HGF precursor protein variant and the protease to cleave the peptide chain X are simultaneously expressed, and the peptide chain X is cleaved by the protease; and

(20) a medicament comprising the active HGF protein variant according to any of the above-mentioned (9) to (14) as an active ingredient.

Effect of the Invention

The HGF precursor protein variant according to the present invention can be converted into an active heterodimer bound by a disulfide (S—S) bond (an active HGF protein variant) under a serum-free condition, and therefore, the risk of contamination of abnormal prions derived from fetal bovine serum can be avoided. Also, according to the invention, an active HGF protein variant can be produced in a serum-free expression system, resulting in low-cost production of an active HGF protein variant, which is an economical advantage. The active HGF protein variant produced according to the invention can be used as an alternative medicament of HGF because the variant has substantially the same action as that of HGF.

BEST MODE FOR CARRYING OUT THE INVENTION

Figure 1:
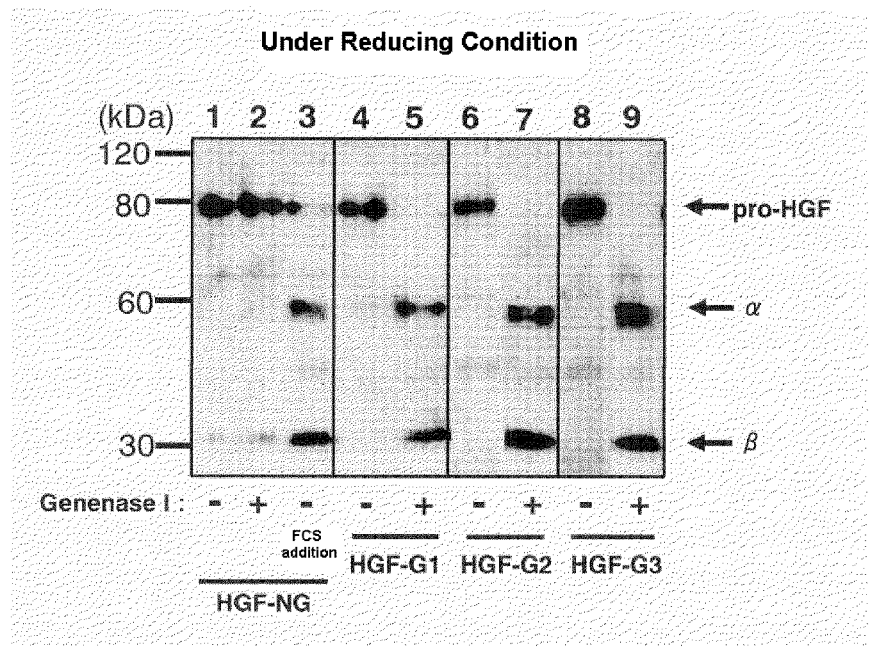
FIG. 1 shows the results of western blot analysis using an anti-HGF polyclonal antibody performed after subjecting the samples of an HGF precursor protein variant treated with or without Genenase I to SDS-PAGE under reducing conditions. In this figure, Pro-HGF represents an HGF-NG precursor protein or an HGF precursor protein variant, α represents the α chain of HGF-NG or the chain of an active HGF protein variant corresponding to the α chain, and β represents the chain of HGF-NG or the chain of an active HGF protein variant corresponding to the β chain.

The present invention will, hereinafter, be described in detail. The peptide chain X inserted between the α chain and the β chain of HGF is not particularly limited as long as the peptide chain has an amino-acid sequence composed of at least two residues, the amino-acid sequence being capable of undergoing peptide cleavage by a protease reaction or a chemical reaction. The number of amino-acid residues which compose peptide chain X is preferably about 20 or less, more preferably about 2 to 10, and most preferably about 2 to 6.

Preferable examples of the amino-acid sequence capable of undergoing peptide cleavage by a protease reaction include a protease recognition sequence (a sequence capable of undergoing peptide cleavage by protease), and the like. The protease recognition sequence is not particularly limited as long as it is recognized by a protease having high substrate specificity. However, it is further preferred that the protease recognition sequence is not included in the amino-acid sequence of HGF. Preferable examples of the protease recognition sequence include His-Tyr or Tyr-His, which is a recognition sequence for Genenase I (Carter, P. et al., Proteins, 6, 240-248 (1989)); Asp-Asp-Asp-Lys (SEQ ID NO: 3), which is a recognition sequence for Enterokinase (Kunitz, M., J. Gen. Physiol. 22, 429-446 (1939), LaVallie, E. R. et al. Journal of Biological Chemistry, 268, 23311-23317 (1993), Vozza, L. A. et al. Biotechnology (NY). 14, 77-81 (1996)); Ile-Glu-Gly-Arg (SEQ ID NO: 4) or Ile-Asp-Gly-Arg (SEQ ID NO: 5), which is a recognition sequence for blood coagulation factor Xa; Leu-Val-Pro-Arg-Gly-Ser (SEQ ID NO: 6), which is a recognition sequence for thrombin; Glu-Xaa-Xaa-Tyr-Phe-Gln-Ser (Xaa represents any amino-acid residue; SEQ ID NO: 7) or Glu-Xaa-Xaa-Tyr-Phe-Gln-Gly (Xaa represents any amino-acid residue; SEQ ID NO: 8), which is a recognition sequence for TEV (tobacco etch virus) protease (Dougherty W G et al., Microbiological Reviews, 57, 781-822 (1992)); Leu-Glu-Val-Leu-Phe-Gln-Gly-Pro (SEQ ID NO: 9), which is a recognition sequence for Rhinovirus 3C protease (Walker P A, et al., Biotechnology (NY), 12 (6), 601-605 (1994)); Arg-Xaa-Lys-Arg (Xaa represents any amino-acid residue; SEQ ID NO: 10) or Arg-Xaa-Arg-Arg (Xaa represents any amino-acid residue; SEQ ID NO: 11), which is a recognition sequence for Furin (Hosaka M, et al., Journal of Biological Chemistry, 266, 12127-12130 (1991)), and the like. His-Tyr or Tyr-His, which is recognition sequence for Genenase I, is particularly preferable because of its shortness. The recognition by Genenase I can be improved by extending the N-terminus of His-Tyr or Tyr-His and thereby converting the His-Tyr or Tyr-His into Pro-Gly-Ala-Ala-His-Tyr (SEQ ID NO: 12) or Pro-Gly-Ala-Ala-Tyr-His (SEQ ID NO: 13), etc. The any amino-acid residue Xaa may be selected from 20 kinds of natural amino acids and unnatural amino acids. The unnatural amino acid may be any compound as long as it has an amino group and a carboxyl group, and for example, it may be a γ-amino butyric acid, etc.

Examples of the amino-acid sequence being capable of undergoing peptide cleavage by a chemical reaction include Asn-Gly cleaved by hydroxylamine reaction, and Asp-Pro cleaved by acetic acid containing guanidine hydrochloride.

The HGF precursor protein variant relating to the present invention can be designed based on the amino-acid sequences of the HGF of human origin or mammal (for example, feline, canine, rat, mouse, bovine, chimpanzee, equine, porcine, sheep, or the like) origin. Examples of the HGF include human-derived HGF (for example, Accession No. NP_001010932, P14210, BAA14348, AAC71655, and the like), mouse-derived HGF (for example, Accession No. AAB31855, NP_034557, BAA01065, BAA01064, and the like), rat-derived HGF (for example, Accession No. NP_58713, and the like), bovine-derived HGF (for example, Accession No. NP_001026921, XP874086, BAD02475, and the like), feline-derived HGF (for example, Accession No. NP_001009830, BAC10545, BAB21499, and the like), canine-derived HGF (for example, Accession No. NP_001002964, BAC57560, and the like), and chimpanzee-derived HGF (for example, Accession No. XP519174, and the like) registered in, for example, the NCBI database or the like, but are not limited thereto. In addition, as long as the HGF has substantially the same action as HGF, one or several (for example about 2 to 30, preferably about 2 to 20, more preferably about 2 to 10, further more preferably 2 to 5; hereinafter the same) amino-acid residues may be substituted, deleted or added in the amino-acid sequence of the HGF. Similarly, a sugar chain may be substituted, deleted or added. Examples of the HGF include HGF (Accession No. NP_001010932), in which 5 amino-acid residues of the HGF registered as Accession No. P14210 are deleted, and the like. Also, when the sequence existing in the inserted peptide chain X and being capable of undergoing peptide cleavage by a protease reaction or a chemical reaction is included in the amino-acid sequence of HGF, as long as the HGF has substantially the same action as HGF, one or several amino-acid residues of the peptide cleavage sequence may be substituted, deleted or added by a known method. Examples of the known method include site-directed mutagenesis described below. With regard to the amino-acid sequence here, "one or several amino-acid residues of the peptide-cleavage sequence may be substituted, deleted, or added" means that a certain number (one or several, the definition of several is same as above) of the amino-acid residues is substituted, deleted or added, with the proviso that the number can be given by a known method such as genetic engineering technique site-directed mutagenesis or naturally. Examples of the HGF where a sugar chain is substituted, deleted or added include an HGF obtained by depriving a natural HGF of a sugar chain by the treatment of an enzyme etc., an HGF having a mutated amino-acid sequence at a glycosylation site to prevent glycosylation, an HGF having a mutated amino-acid sequence to induce glycosylation at a different site from the natural glycosylation site, and the like. Specific examples include an HGF obtained by respectively substituting the 289th Asn with Gln, 397th Asn with Gln, 471th Thr with Gly, 561th Asn with Gln, and 648th Asn with Gln in the glycosylation site of HGF (Accession No. NP_001010932 (SEQ ID NO: 2)) to prevent glycosylation (SEQ ID NO: 14; Fukuta K et al., Biochemical Journal, 388, 555-562 (2005)), and the like. In addition, a protein having at least about 80% homology or more with the amino-acid sequence of HGF, preferably about 90% homology or more, more preferably about 95% homology or more, and having substantially the same action as HGF, is also included in the above-mentioned HGF.

With regard to the above amino-acid sequence, "homology" means, in comparison of primary structures of proteins, the extent of correspondence of amino acids composing each sequence (hereinafter the same).

Specifically, the above HGF may be an amino-acid sequence represented by SEQ ID NO: 1 (Accession No. P14210) or SEQ ID NO: 2 (Accession No. NP_001010932), or the like. Further, examples of the HGF amino-acid sequence of the present invention include an amino-acid sequence represented by SEQ ID NO: 1 or SEQ ID NO: 2 where one or several amino acids are inserted or deleted, where one or more amino acid residues are substituted with another (or more) amino acid residue(s), or where one or more amino acid residues are modified, with the proviso that the amino-acid sequence constitutes a protein which has substantially the same action as HGF. The HGF represented by SEQ ID NO: 2 lacks 5 amino-acid residues from the 162th phenylalanine residue to the 166th serine residue of the amino-acid sequence represented by SEQ ID NO: 1. Therefore, the HGF represented by SEQ ID NO: 2 may be called 5-amino-acid-deleted-type human HGF. The inserted or substituted amino-acid residue may be unnatural amino acids other than 20 kinds of natural amino acids encoded by DNA. The unnatural amino acid may be any compound as long as it has an amino group and a carboxyl group, and for example, it may be a γ-amino butyric acid, etc. Also, examples of the HGF amino-acid sequence of the present invention include an amino-acid sequence having at least about 80% or more, preferably about 90% or more, more preferably about 95% or more homology with the amino-acid sequence represented by SEQ ID NO: 1 or SEQ ID NO: 2, and having substantially the same action as HGF. The amino-acid sequence having at least about 805 homology or more with the amino-acid sequence represented by SEQ ID NO: 1 or SEQ ID NO: 2 may be the HGF amino-acid sequence registered as Accession No. NP_001010934, BAA14348, AAC71655, AAB31855, NP_034557, BAA01065, BAA01064, NP_58713, NP_001026921, XP874086, BAD02475, NP_001009830, BAC10545, BAB21499, NP_001002964, BAC57560, XP519174 or the like in the NCBI database or the like, but not limited thereto.

The HGF precursor protein variant according to the present invention can be produced by a method comprising the following steps 1 to 4, but steps are not limited thereto as long as the HGF precursor protein variant can be produced.

Step 1:

In Step 1, DNA encoding HGF precursor protein variant is prepared. The step includes a step to prepare a recombinant expression vector including DNA encoding HGF precursor protein variant by inserting the peptide chain X between the α chain and the β chain of HGF.

The insertion of the peptide chain X between the α chain and the β chain of HGF may be only inserting the peptide chain X into the boundary between the α chain and the β chain of a natural HGF. In this case, the total number of amino-acid residues of the HGF is increased by the number of the amino-acid residues included in the inserted sequence. Also, the insertion may be inserting the peptide chain X into the region at either side of the boundary between the α chain and the β chain of HGF where about 1 to 20 amino-acid residues from the C-terminus of the α chain and/or about 1 to 20 amino-acid residues from the N-terminus of the β chain are deleted.

The α chain and the β chain of HGF may be, for example, the α chain consisting of from the 32nd to the 494th of the amino-acid sequence represented by SEQ ID NO: 1 and the β chain consisting of from the 495th to the 728th of the amino-acid sequence represented by SEQ ID NO: 1; or the α chain consisting of from the 32nd to the 489th of the amino-acid sequence represented by SEQ ID NO: 2 and the β chain consisting of from the 490th to the 723rd of the amino-acid sequence represented by SEQ ID NO: 2. The amino-acid residues constituting the boundary between the α chain and the β chain are, for example, in the case of the HGF represented by SEQ ID NO: 1, the arginine at the 494th and the valine at the 495th. The amino-acid residues constituting the boundary between the α chain and the β chain are, for example, in the case of the 5-amino-acid-deleted-type human HGF represented by SEQ ID NO: 2, the arginine at the 489th and the valine at the 490th.

The insertion of the peptide chain X between the α chain and the β chain of HGF can be performed by site-directed mutagenesis of protein or the like. The mutagenesis method may be, for example, inserting a base sequence encoding the aimed peptide chain X into the base-sequence region at the boundary between the DNA encoding the α chain and the DNA encoding the β chain of HGF, or introducing a mutation to induce substitution for an aimed sequence. The method to mutagenize a base sequence may be, for example, synthesizing a mutant primer corresponding to the site to mutate, and then employing a known method, for example, the Kunkel method (Kunkel, T. A. Proc. Natl. Acad. Sci. U.S.A. 82, 488-492 (1985)), etc. By using a commercially-available mutagenesis kit or the like, mutation can be easily introduced. Examples of the mutagenesis kit include, for example, GeneMorph Random Mutagenesis Kit (made by Stratagene) containing Mutazyme DNA polymerase, GeneTailor (Trademark) Site-Directed Mutagenesis System (made by Invitrogen), Mutan (Trademark)-Super Express Km (made by Takara Bio), QuikChange (Trademark) XL Site-Directed Mutagenesis Kit (made by Toyobo), GeneEditor in vitro Site-Directed Mutagenesis System (made by Promega), and the like, but are not limited thereto. The DNA mutated by the above-mentioned Kunkel method or with the mutagenesis kit, etc. (DNA having a base sequence encoding HGF precursor protein variant; hereinafter referred to as DNA encoding HGF precursor protein variant) can be excised by a restriction enzyme from a plasmid or phage that has produced the DNA through mutation and/or amplification. The excised DNA may be purified by a known method, or directly inserted into an appropriate expression vector described below. The purification may be performed using a commercially-available kit, for example, QIAquick Gel extraction Kit (made by Qiagene), S.N.A.P. UV-Free Gel Purification Kit (made by Invitrogen), or the like, but the kit is not limited thereto. The DNA encoding HGF precursor protein variant can also be produced by a known chemical synthetic method. Examples of the chemical synthetic method include chemical synthesis using a DNA synthesizer such as DNA synthesizer adopting the phosphoramidite method.

The expression vector having DNA encoding HGF precursor protein variant can be produced by ligating a DNA encoding HGF precursor protein variant to downstream of a promoter in an appropriate vector for HGF expression using a restriction enzyme and DNA ligase. The recombinant expression vector contains a promoter, a ribosome binding site, an initiation codon, a termination codon, a terminator, and the like, as needed. It is preferred that the recombinant expression vector is constructed to contain (1) a promoter, (2) a ribosome binding site, (3) an initiation codon, (4) a DNA encoding HGF precursor protein variant of the present invention, (5) a termination codon and (6) a terminator in order toward downstream of transcription. The expression vector used in the present invention may be, when the host is *Escherichia coli*, a plasmid of pBR322, pUC18, pUC19 (made by Toyobo), or the like; when the host is *Bacillus subtilis*, a plasmid of pUB110 (made by Sigma), or the like; and when the host is yeast, a plasmid of pYES2 (made by Invitrogen), pRB15 (ATCC37062), or the like. A vector for an animal cell may be pCAGGS and pCXN2 (Niwa, H., Yamamura, K. and Miyazaki, J., Gene, Vol. 108, pp. 193-200 (1991) and JP-A No. 3-168087) or pcDL-SRα (Takebe, Y. et al., Mol. Cell. Biol., Vol. 8, pp. 466-472 (1988)) or the like. Besides, the expression vector may be bacteriophage λgt10 or λgt11 (made by Stratagene), virus SV40 (made by BRL), BPV (ATCC VR-703), or a vector derived from retroviral gene, but not limited thereto. Any vector may be used as long as it can be replicated and/or amplified in a host.

The promoter and the terminator are not also particularly limited as long as they are corresponding to the host used for expression of DNA encoding the aimed HGF precursor protein variant. Examples of the promoter include, when the host is *Escherichia coli*, trp promoter, lac promoter, recA promoter, λPL promoter, lpp promoter, and the like; and when the host is yeast, PHO5 promoter, PGK promoter, GAP promoter, ADH promoter, and the like. When the host is an animal cell, in addition to SRα promoter; CAG promoter; a promoter obtained from viral genome of Rous sarcoma virus (RSV), MPSV, polyoma virus, fowlpox virus, adenovirus, bovine papilloma virus, fowl sarcoma virus, cytomegalovirus (CMV), hepatitis B virus, simian virus 40 (SV40), and vaccinia virus; metallo-thioneine promoter; heat shock promoter; or the like is included. In the case of using a higher mammal host, an enhancer is preferably introduced into a vector. Introduction of an enhancer may increase transcription. The enhancer may be SV40 enhancer, initial promoter/enhancer of cytomegalovirus, polyoma enhancer, adenovirus enhancer, or the like. The terminator may be, when the host is *Escherichia coli*, trp terminator, lpp terminator, or the like; when the host is *Bacillus subtilis*, amyF terminator or the like; when the host is yeast, CYC1 terminator or the like; or when the host is an animal cell, SV40 terminator, HSV1TK terminator, or the like. These promoters and terminators are appropriately combined depending on the host used.

Step 2:

In Step 2, HGF precursor protein variant is synthesized. The step includes a step to produce a transformant by introducing the recombinant expression vector prepared in the Step 1 into a host, and then synthesize HGF precursor protein variant in the transformant.

The recombinant expression vector having DNA encoding HGF precursor protein variant, the vector which has been prepared in the Step 1, is introduced into a host, by a competent cell method (J. Mol. Biol., vol. 53, p. 154, (1970)), protoplast method (Proc. Natl. Acad. Sci. USA, vol. 75, p. 1929 (1978)), calcium phosphate method (Science, vol. 221, p. 551 (1983)), DEAE dextran method (Science, vol. 215, p. 166 (1982)), electric pulse method (Proc. Natl. Acad. Sci. USA, vol. 81, p. 7161 (1984)), in vitro packaging method (Proc. Nat. Acad. Sci. USA, vol. 72, p. 581 (1975)), viral vector method (Cell, vol. 37, p. 1053 (1984)), micro injection method (Exp. Cell. Res., vol. 153, p. 347 (1984)), or the like, to produce a transformant.

The cell which can be used as a host is not particularly limited, and eukaryotic cells such as an animal, a plant, an insect, a eukaryotic microorganism, or the like; or prokaryotic cells such as a prokaryotic microorganism or the like, may be used. These cells may form an individual, and a host may be an animal individual, a plant individual, or an insect individual. The eukaryotic cell may be an adherent cell or a floating cell, for example, may be a eukaryotic cell producing HGF precursor protein variant and accumulating it in the cell, or a eukaryotic cell producing HGF precursor protein variant and secreting it out of the cell. The animal cell may be, for example, a CHO cell (Chinese hamster ovary cell), a COS cell, a BHK cell, a mouse C127 cell, a Hela cell, or the like. The plant cell may be, for example, cells of rice, tobacco, *Arabidopsis thaliana*, or the like, and the insect cell may be, for example, Sf9 cell, Sf21 cell, or the like. The insect individual may be, for example, silk worm (*Bombyx mori*). The eukaryotic microorganism may be, yeast such as *Saccharomyces cerevisiae, Schizosaccharomyces pombe, Candida boidinii*, or *Pichia pastoris*; or a filamentous fungus such as *Aspergillus, Trichoderma* or *Mucor*. The prokaryotic microorganism may be, *Escherichia coli, Bacillus subtilis*, or the like.

The resultant transformant is preferably cultured in a medium appropriate for the host for the purpose of producing an aimed HGF precursor protein variant. The medium contains a carbon source, a nitrogen source, inorganic substances, vitamins, serum, agents, and the like, necessary for growth of the transformant. When the host of the transformant is *Escherichia coli*, the medium may be LB medium (Nissui Pharmaceutical Co., Ltd.), M9 medium (J. Exp. Mol. Genet., Cold Spring Laboratory, New York, p. 431 (1972)), or the like. When the host is yeast, the medium may be YEPD medium (Genetic Engineering, vol. 1, Plenum Press, New York, p. 117 (1979)) or the like. When the host is an animal cell, the medium may be MEM medium (Minimum Essential Medium), DMEM medium (Dulbecco's Modified Eagle's Medium), RPMI 1640 medium (Nissui Pharmaceutical Co., Ltd.) containing 20% or less by volume of fetal bovine serum, or the like. A transformant is usually cultured at a temperature of 20 to 45° C. and a pH of 5 to 8, with ventilation or stirring as required. When the host is an animal adherent cell or the like, carriers such as glass beads, collagen beads or acetyl cellulose hollow fiber can be preferably used. A transformant can be cultured even with any other medium composition or under other culturing conditions as long as the transformant can grow, and therefore, the composition and culturing conditions are not limited to the above-mentioned examples.

The obtained transformant can express DNA encoding HGF precursor protein variant and synthesize HGF precursor protein variant.

Further, the HGF precursor protein variant of the present invention can be obtained also by a cell-free protein synthesis system. The cell-free protein synthesis system includes a method of synthesizing protein not using a live cell but using DNA or mRNA encoding the aimed protein as a template, by using cell extract prepared from *Escherichia coli*, rabbit reticulocyte, wheat germ, or the like; or by using protein synthesis factors contained in the cell extract solution. Since a cell extract solution contains molecules necessary for protein synthesis such as ribosome, tRNA, and translation factors, adding an energy source such as ATP and GTP; and substrate amino acids thereto synthesizes a protein. Instead of the cell extract solution, a mixture of protein synthesis factors contained in the cell extract solution may be used.

Step 3:

In Step 3, HGF precursor protein variant (hereinafter also referred to just as precursor) is converted into an active HGF protein variant.

Since the HGF precursor protein variant synthesized in the Step 2 is inactive, it is preferable to convert the precursor into an active HGF protein variant by cleaving the precursor to convert it into a double-stranded chain by cleaving at least one site of the peptide chain X inserted between the α chain and the β chain.

The cleaving method is not particularly limited as long as a specific amino-acid sequence in the peptide chain X on the precursor is cleaved. The method includes, for example, a protease treatment or a chemical treatment.

The protease capable of cleaving a specific amino-acid sequence is not particularly limited, and preferably used is, for example, Genenase I, Enterokinase, blood coagulation factor Xa, thrombin, TEV protease, Rhinovirus 3C protease, Furin, or the like, which has a high substrate specificity to recognize a specific amino-acid sequence. For example, when a precursor has an inserted Genenase I recognition sequence, the single-stranded precursor can be activated by the action of Genenase I. In this case, the cleavage occurs between His-Tyr or Tyr-His, which is a Genenase I recognition sequence. When a precursor has an inserted Enterokinase recognition sequence, the single-stranded precursor can be activated by the action of Enterokinase. In this case, the cleavage occurs at the C-terminus of the lysine residue of Asp-Asp-Asp-Lys (SEQ ID NO: 3), which is an Enterokinase recognition sequence. Similarly, when a precursor has an inserted recognition sequence for blood coagulation factor Xa, the single-stranded precursor can be activated by the action of blood coagulation factor Xa. In this case, the cleavage occurs between Gly-Arg in the Ile-Glu-Gly-Arg (SEQ ID NO: 4) or Ile-Asp-Gly-Arg (SEQ ID NO: 5), which is a recognition sequence for blood coagulation factor Xa. When a precursor has an inserted thrombin recognition sequence, the single-stranded precursor can be activated by thrombin. In this case, the cleavage occurs between Arg-Gly of the Leu-Val-Pro-Arg-Gly-Ser (SEQ ID NO: 6), which is a thrombin recognition sequence. When a precursor has an inserted TEV protease recognition sequence, the single-stranded precursor can be activated by the action of TEV protease. In this case, the cleavage occurs at the C-terminus of the serine residue of Glu-Xaa-Xaa-Tyr-Phe-Gln-Ser (SEQ ID NO: 7), which is a TEV protease recognition sequence, or at the Glu-Xaa-Xaa-Tyr-Phe-Gln-Gly (SEQ ID NO: 8), which is also a TEV protease recognition sequence. When a precursor has an inserted Rhinovirus 3C protease recognition sequence, the single-stranded precursor can be activated by Rhinovirus 3C protease. In this case, the cleavage occurs between Gln-Gly of the Leu-Gln-Val-Leu-Phe-Gln-Gly-Pro (SEQ ID NO: 9), which is a Rhinovirus 3C protease recognition sequence. When a precursor has an inserted Furin recognition sequence, the single-stranded precursor can be activated by Furin. In this case, the cleavage occurs at the C-terminus of the C-terminal arginine residue of Arg-Xaa-Lys-Arg (SEQ ID NO: 10) or Arg-Xaa-Arg-Arg (SEQ ID NO: 11), which is a Furin recognition sequence.

The protease includes a protease isolated from a living body, cells or fungus and then purified, a protease purified as a recombinant protein, or a commercially-available protease. The protease may be added to the above-mentioned medium for a transformant, or reacted with HGF precursor protein variant extracted from a transformant or the like and then purified.

Examples of other methods to react a protease with HGF precursor protein variant include a method where DNA encoding a protease is also implanted into the transformant producing HGF precursor protein variant in order to allow the transformant to express the protease and HGF precursor protein variant at the same time. In this case, it is preferred that the DNA to be implanted is capable of encoding a protease recognizing the protease recognition sequence included in the peptide chain X. Since the transformant produces the protease and HGF precursor protein variant at the same time, the HGF precursor protein variant produced by the transformant can be automatically cleaved at the site of protease recognition sequence in the peptide chain X and activated.

Examples of the method to cleave the peptide chain X site in HGF precursor protein variant by a chemical treatment include a method to react a chemical treatment agent such as hydroxylamine or acetic acid containing guanidine hydrochloride (preferably, for example, about 10% by volume acetic acid containing about 7 M guanidine hydrochloride (approximately pH 2.5)) with HGF precursor protein variant. Protein cleavage can occur when, for example, Asn-Gly binding is cleaved by the reaction of hydroxylamine, or when Asp-Pro binding is cleaved by acetic acid containing guanidine hydrochloride. The above-mentioned chemical treatment agent may be added to the above-mentioned medium for a transformant, as long as the transformant can grow.

The protease treatment or the chemical treatment may be performed in the presence of, for example, a reducing agent (for example, dithiothreitol (DTT), β-mercaptoethanol, or the like) or a denaturation agent (for example, SDS, urea, guanidine hydrochloride, or the like). In this case, it is preferred that a renaturation reaction is performed after the peptide chain X is cleaved. The renaturation reaction may be performed according to a known method, for example, a method described in Molecular Cloning: A Laboratory Manual. 3rd Edition. Sambrook, J. and Russell, D. W., eds. (2001) Cold Spring Harbor Press, pp. A4. 39.

Step 4:

In Step 4, an active HGF precursor protein variant is isolated and purified. The active HGF precursor protein variant produced in the culture supernatant of a transformant or in a transformant can be isolated and purified by a known salting out method, solvent precipitation method, dialysis method, ultrafiltration method, gel electrophoresis method or gel filtration chromatography, ion exchange chromatography, reverse phase chromatography, affinity chromatography, or the like, or by a combination thereof. Particularly, a combination of a salting out method using ammonium sulfate, S-sepharose ion chromatography, heparin sepharose affinity chromatography and phenylsepharose hydrophobic chromatography; and a combination of a salting out method using ammonium sulfate, S-sepharose ion chromatography and anti-HGF antibody sepharose affinity chromatography; and the like, are preferable and effective purification methods.

The active HGF precursor protein variant of the present invention has substantially the same action as HGF, and therefore, like HGF, can be used as a protein medicament, namely as a therapeutic drug or a preventive drug for various diseases of human and other mammals (canine, feline, rat, mouse, rabbit, horse, bovine, sheep, guinea pig, and the like). Examples of the uses thereof include a liver disease drug, a renal disease drug, a wound healing drug, a cutaneous ulcer drug, a hair root cell proliferating drug, an anticancer drug, a lung disease drug, and an anti-side-effect drug for cancer therapy. More specifically, the active HGF precursor protein variant is useful for preventing and/or treating diseases to which HGF is applicable, including liver diseases (for example, hepatitis, cirrhosis, liver failure, liver regeneration after surgery, and the like), renal disease (for example, glomerular nephritis, kidney failure, nephrogenic anemia, diabetic nephropathy, kidney disorder after drug administration, and the like), cutaneous diseases (for example, white spot lesion, burn injury, bedsore, cutaneous ulcer, calvities, and the like), blood diseases (for example, thrombocytopenia, bone marrow transplantation, and the like), eye diseases (for example, corneal ulcer, and the like), lung diseases (for example, pneumonia, emphysema, pulmonary tuberculosis, chronic obstructive lung disease, pneumoconiosis, fibroid lung, and the like), gastroduodenal diseases (for example, gastric inflammation, gastric ulcer, duodenal ulcer, and the like), cancers and related diseases (for example, various cancers; side effects of cancer therapy such as liver toxicity, kidney toxicity, nausea, vomit, thrombocytopenia, hair loss; and the like), bone diseases (for example, osteoporosis, osteodysplasty, osteoarthritis, and the like), and central nervous system diseases (for example, abnormal neural differentiation, and the like).

The medicinal preparation containing the active HGF precursor protein variant of the present invention is used in the form of a general medicinal preparation. As the form of the medicinal preparation, various dosage forms (for example, liquid, solid, capsule, and the like) may be adopted. In general, the active HGF precursor protein variant as an active ingredient and binding substances are sorely used or used in combination with a customary carrier to give an injection, inhalant, suppository or oral agent, and an injection is preferable. The injection may be an aqueous or oily injection. The injection can be prepared by a known method. For example, an aqueous injection can be prepared as follows: to an aqueous solvent such as water for injection and purified water, optionally added is a pharmaceutically acceptable excipient, for example a tonicity agent (such as sodium chloride, potassium chloride, glycerin, mannitol, sorbitol, boric acid, borax, glucose, propylene glycol), a buffering agent (such as phosphate buffer solution, acetate buffer solution, borate buffer solution, carbonate buffer solution, citrate buffer solution, Tris-buffer solution, glutamic acid buffer solution, epsilon-aminocaproic acid buffer solution), a preservative (such as methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edetate, boric acid, borax), a thickener (such as hydroxyethyl cellulose, hydroxypropyl cellulose, polyvinyl alcohol, polyethylene glycol), a stabilizer (such as albumin, globulin, gelatine, alanine, glycine, mannitol, glucose, dextran, sorbitol, ethylene glycol, sodium bisulfite, sodium thiosulfate, sodium edetate, sodium citrate, ascorbic acid, dibutyl hydroxytoluene), a pH adjuster (such as hydrochloric acid, sodium hydroxide, phosphoric acid, acetic acid) or the like. Next, after the active HGF precursor protein variant is dissolved in the resulting solution, the solution is sterile-filtered through a filter or the like. Finally, the filtered solution is filled into a sterile container. Additionally, an appropriate solubilizing agent, for example an alcohol (such as ethanol), a polyalcohol (such as propylene glycol and polyethylene glycol), a nonionic surfactant (such as polysorbate 80 and polyoxyethylene (50) hydrogenated castor oil) or the like may be also incorporated. To prepare an oily injection, sesame oil, soy bean oil or the like may be used as an oily solvent and benzyl benzoate, benzyl alcohol or the like may be incorporated as a solubilizing agent. The prepared injection is usually filled into an appropriate ampule or vial, etc. The injection is prepared in an amount of the active HGF precursor protein variant ranging usually from about 0.0002 to 3% by mass, preferably about 0.001 to 2% by mass. It is preferred that a liquid preparation such as an aqueous injection is frozen for preservation or stored after removing moisture by lyophilization or the like. The lyophilized preparation can be used by adding distilled water for injection or the like as needed and redissolving the preparation.

The oral drug is formulated into for example, a tablet (including sugarcoated tablet, filmcoated tablet, and enteric tablet), granule, fine granule, powder, soft or hard capsule (including enteric capsule), liquid, emulsion, suspension, syrup or the like. These preparations can be prepared by an ordinary method for preparation.

The active HGF precursor protein variant to be used in the present invention together with a biodegradable polymer can be prepared in the form of a sustained-release preparation, for example, a depot preparation. Especially, a depot preparation of the active HGF precursor protein variant can be expected to reduce the dose frequency, prolong the effect and reduce the side effect, etc. The sustained-release preparation can be prepared by known methods. The biodegradable polymer to be used in the sustained-release preparation can be appropriately selected from known biodegradable polymers, for example, a polysaccharide such as starch, dextran or chitosan; a protein such as collagen or gelatin; a polyamino acid such as polyglutamic acid, polylysine, polyleucine, polyalanine or polymethionine; a polyester such as polylactic acid, polyglycolic acid, lactic acid-glycolic acid copolymer, polycaprolactone, poly-β-hydroxybutyric acid, polymalic acid, polyanhydride or fumaric acid-polyethylene glycol-vinylpyrrolidone copolymer; a polyalkyl cyanoacrylate such as a polyortho ester or polymethyl-α-cyanoacrylate; or a polycarbonate such as polyethylene carbonate or polypropylene carbonate. Preferred is a polyester and more preferred is polylactic acid or lactic acid-glycolic acid copolymer. When lactic acid-glycolic acid copolymer is used as a biodegradable polymer, the proportion based on the mole percentage (lactic acid/glycolic acid) depends on the duration of sustained release. For example, when the duration of sustained release is from about 2 weeks to 3 months, preferably from about 2 weeks to 1 month, the preferable proportion is from about 100/0 to 50/50. In general, the weight-average molecular weight of the polylactic acid or lactic acid-glycolic acid copolymer is preferably from about 5,000 to 20,000. The polylactic acid or lactic acid-glycolic acid copolymer can be prepared by known synthesis methods, for example the method disclosed by JP-A No. 61-28521. The proportion of the active HGF precursor protein variant to the biodegradable polymer is not particularly limited, but a preferable example of the proportion is from about 0.01 to 30% by mass of the active HGF precursor protein variant relative to the biodegradable polymer.

The inhalant can also be prepared according to normal means for preparation. The amount of the active HGF precursor protein variant in a preparation can be appropriately adjusted depending on dosage form, disease to be treated and the like.

A spray can also be prepared according to normal means for preparation. To prepare a spray, any excipient may be incorporated into the spray as long as the excipient is usually used for an inhaled preparation. For example, in addition to a propellant, the above-mentioned solvent, preservative, stabilizer, tonicity agent or pH adjuster, etc. can be incorporated. Examples of the propellant include a liquefied gas propellant and a compressed gas. Examples of the liquefied gas propellant include a fluorohydrocarbon such as a substitute for chlorofluorocarbons (HCFC22, HCFC-123, HCFC-134a, HCFC142 or the like), liquefied petroleum, dimethylether or the like. Examples of the compressed gas include a soluble gas such as carbon dioxide gas and nitrous oxide gas or an insoluble gas such as nitrogen gas.

The suppository can also be prepared by an ordinary method for preparation using a conventional base (for example, cacao butter, lauric butter, glycerogelatine, Macrogol, Witepsol and the like). In formulation, a stabilizer is preferably added. In addition, a preparation of the present invention may contain other essential excipients, for example, fillers, solubilizers, antioxidants, soothing agents, isotonic agents, or the like.

The preparation of the present invention can be administered via a suitable administration route corresponding to its dosage form. For example, it can be formed into an injection and administered intravenously, intraarterially, subcutaneously, intramuscularly, or the like. The dose thereof is appropriately adjusted depending on disease, symptom, age, body weight or the like of a patient, and for example, it is from 0.01 mg to 500 mg of HGF for an adult, preferably from 0.05 mg to 100 mg, more preferably from 0.05 mg to 50 mg, and most preferably from 0.05 mg to 20 mg. This dose is preferably administered once or in several divided portions daily.

The present invention will hereinafter be described in more detail by the following examples, but the scope of the invention is not limited thereto.

The meanings of abbreviations used in the examples are shown below.
HGF: hepatocyte growth factor
LB medium: Luria-Bertani medium
DMEM medium: Dulbecco's Modified Eagle's Medium
Amp: ampicillin
FCS: fetal calf serum
Tris: tris(hydroxymethyl) aminomethane
Tween 80: polyoxyethylene (20) sorbitan monooleate
SDS: sodium dodecylsulfate
PAGE: polyacrylamide gel electrophoresis
PVDF: polyvinylidene fluoride
A: Adenine
C: Cytosine
G: Guanine
T: Thymine
Ala: Alanine
Arg: Arginine
Gly: Glycine
Gln: Glutamine
Lys: Lysine
Thr: Threonine
Leu: Leucine
His: Histamine
Tyr: Tyrosine
Pro: Proline
Also, "%" means % by mass unless otherwise stated.

Example 1

To the both ends of the base sequence encoding the HGF represented by SEQ ID NO: 14 (5-amino-acid-deleted-type/glycosylation-deficient human HGF; HGF having a natural α chain-β chain boundary sequence Arg (489th)-Val (490th) and having a mutation at a glycosylation site; hereinafter referred to as HGF-NG) (SEQ ID NO: 15), a base sequence including BamHI recognition sequence (GGATCC) and a base sequence including XbaI recognition sequence (TCTAGA) were added, and this sequence was incorporated between the BamHI site and the XbaI site of pcDNA3.1 (+) vector (made by Invitrogen). The obtained vector is called pcDNA-dHGF-NG.

As variants having an introduced Genenase I recognition sequence (His-Tyr) at the α chain-β chain boundary of HGF-NG, a variant where the two C-terminal residues (Leu-Arg) of the HGF α chain were converted into His-Tyr (referred to as HGF-G1), a variant where the C-terminal residue (Arg) of the HGF α chain was converted into Tyr and the N-terminal residue (Val) of the HGF β chain was converted into His (referred to as HGF-G2), and a variant where the six C-terminal residues (the 484th to 489th of the SEQ ID NO: 14; Lys-Thr-Lys-Gln-Leu-Arg) of the HGF α chain were converted into Pro-Gly-Ala-Ala-His-Tyr (SEQ ID NO: 12) (referred to as HGF-G3), were prepared as follows.

First, vectors for expressing HGF-G1, HGF-G2 and HGF-G3 were prepared. For this purpose, using the above-mentioned pcDNA-dHGF-NG as a template, a base sequence region encoding the HGF α chain-β chain boundary was mutated by the Kunkel method, and the mutated chain was amplified. Specifically, to prepare vectors to express HGF-G1, HGF-G2, and HGF-G3, the primer of the SEQ ID NO: 16 (5'-phosphorylated), the primer of the SEQ ID NO: 17 (5'-phosphorylated), and the primer of the SEQ ID NO: 18 (5'-phosphorylated), were used respectively. The mutated chain was elongated and amplified using pcDNA-dHGF-NG as a template and KOD Plus (made by Toyobo) as DNA polymerase. Then, after the template DNA was digested by DpnI treatment, the remaining mutated chain was used for transformation of *Escherichia* DH5α competent cells (made by Nippon Gene) by the calcium chloride method to prepare the desired mutated vector.

TABLE 1

| Primer | Sequence listing |
|---|---|
| 5'-CCAAAACGAAACAACACTATGTTGTAAATGGGATTCCAACACG-3' | SEQ ID NO: 16 |
| 5'-CGAAACAATTGTATCACGTAAATGGGATTCCAACACG-3' | SEQ ID NO: 17 |
| 5'-GTAATATCTTGTGCCCCAGGGGCCGCACACTATGTTGTAAATGG-3' | SEQ ID NO: 18 |

On LB/Amp plates, Amp-resistant colonies were picked, and each mutated vector was extracted from each obtained clone using QIAprep Spin Miniprep Kit (made by Qiagen). By analyzing the base sequence encoding HGF-NG in each mutated vector, the target clone was chosen. Specifically, the base sequence region encoding the HGF represented by the SEQ ID NO: 14 in a mutated vector was subjected to sequence reaction using Big Dye Terminator v3.1 Cycle Sequence Kit (made by Applied Biosystems), and then analyzed with 3100 Genetic Analyzer (made by Applied Biosystems). A vector of which the HGF-NG α chain-β chain boundary was confirmed to be successfully mutated was chosen and used in later experiments.

The mutated vector where the Leu-Arg at the 488th to 489th of the SEQ ID NO: 14 is substituted with His-Tyr by using the mutated primer of the SEQ ID NO: 16 is referred to as pcDNA-dHGF-NG-G1. The mutated vector where the Arg-Val at the 489th to 490th of the SEQ ID NO: 14 is substituted with Tyr-His by using the mutated primer of the SEQ ID NO: 17 is referred to as pcDNA-dHGF-NG-G2. The mutated vector where the Lys-Thr-Lys-Gln-Leu-Arg at the 484th to 489th of the SEQ ID NO: 14 is substituted with Pro-Gly-Ala-Ala-His-Tyr by using the mutated primer of the SEQ ID NO: 18 is referred to as pcDNA-dHGF-NG-G3.

Next, pcDNA-dHGF-NG and each mutated vector (pcDNA-dHGF-NG-G1, pcDNA-dHGF-NG-G2 and pcDNA-dHGF-NG-G3), were respectively transfected into Human embryonic kidney 293T cells (DuBridge R B, et al., Molecular Cellular Biology, 7, 379-387 (1987)). For the transfection, the 293T cells were precultured in the Dulbecco's Modified Eeagle's Medium (DMEM) to which 10% by volume of fetal calf serum (FCS) is added. This DMEM was replaced with the serum-free DMEM just before transfection, and transfection was performed by the lipofection method using LIPOFECTAMINE 2000 (made by Invitrogen). After transfection was complete, the culture in the serum-free DMEM was continued, and 6 hours after the transfection, heparin was added to a concentration of 1 μg/mL. The culture was further continued for three days to allow HGF-NG precursor protein or HGF precursor protein variant (the HGF-G1 precursor protein, HGF-G2 precursor protein, or HGF-G3 precursor protein) produced by each vector to accumulate in the serum-free DMEM, respectively. Three days after, the DMEM was collected from three petri dishes respectively, mixed, filtered through a 0.22 μm filter, and kept at −80° C. until being purified. The concentration of the HGF-NG precursor protein, HGF-G1 precursor protein, HGF-G2 precursor protein, or HGF-G3 precursor protein was analyzed by ELISA. The ELISA method was performed by using the Immunis kit (made by Institute of Immunology) in accordance with the protocol described in the kit.

The above-mentioned medium was thawed and filtered again through a 0.22 μm filter. To this, Heparin Sepharose resin (made by Amersham Biosciences) equilibrated with 50 mM Tris-HCL (pH 7.5), 0.01% Tween 80 and 0.3 M NaCl was added in order to allow the HGF-NG precursor protein, HGF-G1 precursor protein, HGF-G2 precursor protein, or HGF-G3 precursor protein to bind to the resin at room temperature. The resin was then washed with 50 mM Tris-HCL (pH 7.5), 0.01% Tween 80 and 0.3 M NaCl and the HGF-NG precursor protein, HGF-G1 precursor protein, HGF-G2 precursor protein, or HGF-G3 precursor protein was eluted with 50 mM Tris-HCL (pH 7.5), 0.01% Tween 80 and 2 M NaCl for partial purification.

To the HGF-NG precursor protein, HGF-G1 precursor protein, HGF-G2 precursor protein, or HGF-G3 precursor protein (200 ng each) partially purified with the heparin resin, half the amount (100 ng) of Genenase I (made by New England Laboratory) was added. The mixture was treated in 50 mM Tris-HCL (pH 7.5), 0.01% Tween 80 and 2 M NaCl at 25° C. for 12 hours. Meanwhile, HGF-NG precursor protein having a natural α chain-β chain boundary sequence, to which any Genenase I recognition sequence was not inserted, was incubated in 50 mM Tris-HCL (pH 7.5), 0.01% Tween 80 and 2 M NaCl with 1% by volume of FCS added thereto at 37° C. for 12 hours.

Each active HGF precursor protein variant (active HGF-G1, active HGF-G2, or active HGF-G3) obtained after Genenase I treatment was subjected to the Western blot under reducing or nonreducing condition as follows.

Western blot: Active HGF-G1, active HGF-G2, or active HGF-G3 after Genenase I treatment was subjected to SDS-PAGE under reducing condition (in the presence of 100 mM DTT) or nonreducing condition, and transferred onto PVDF membrane. The protein transferred onto the PVDF membrane was detected using, as a probe, human HGF polyclonal antibody prepared by immunizing a rabbit with human HGF (Matsumoto K, et al., Proceedings for National Academy of Science of the United States of America, 89, 3800-3804 (1992)).

FIG. 1 shows the results of western blot analysis in the SDS-PAGE under reducing condition. With regard to HGF-NG precursor protein having a natural α chain-β chain boundary sequence, to which any Genenase I recognition sequence was not inserted, Genenase I treatment did not affect band positions. In either case of treatment with or without Genenase I, a band was found at the position of single-stranded HGF-NG precursor protein (Lanes 1 and 2 in FIG. 1). From this, it was confirmed that HGF-NG precursor protein having a natural α chain-β chain boundary sequence was not cleaved by Genenase I. Meanwhile, after FCS was added to this HGF-NG precursor protein and the protein was treated at 37° C. for 12 hours, two bands of α chain and β chain were detected, which confirmed that the protein was activated (Lane 3). In each case of HGF-G1 precursor protein, HGF-G2 precursor protein, and HGF-G3 precursor protein to which a Genenase I recognition sequence was inserted, without Genenase I treatment, a band was found at the same position as the single-stranded HGF-NG precursor protein (Lanes 4, 6 and 8 in FIG. 1). However, after Genenase I treatment, bands were detected at the same positions as those of the α chain and β chain of HGF-NG (Lanes 5, 7 and 9 in FIG. 1), which confirmed that each protein was converted into a double-stranded structure.

Figure 2:
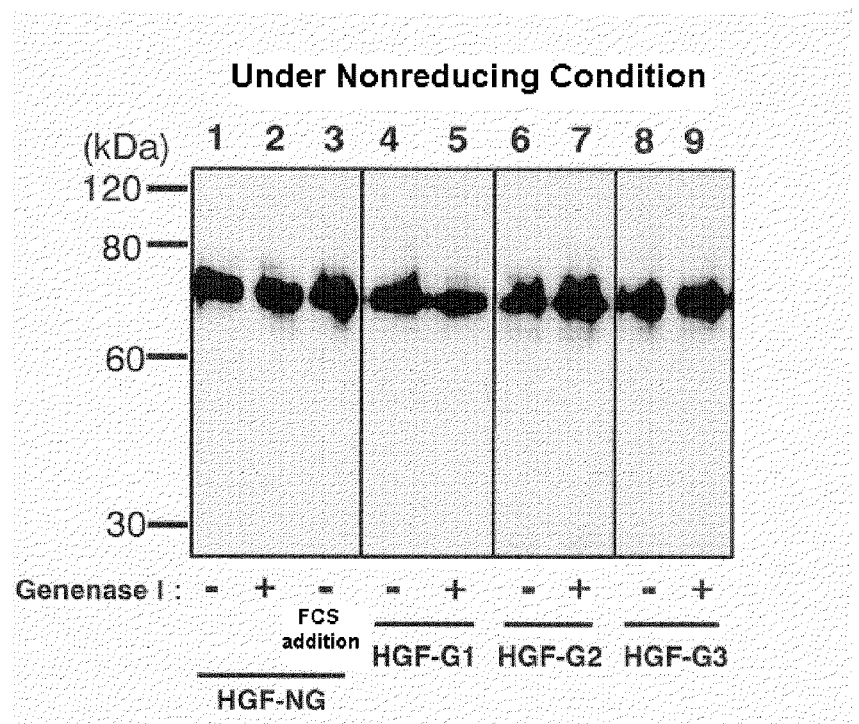
FIG. 2 shows the results of western blot analysis using an anti-HGF polyclonal antibody performed after subjecting the samples of an HGF-NG precursor protein and an HGF precursor protein variant treated with (+) or without (−) Genenase I to SDS-PAGE under nonreducing conditions.

FIG. 2 shows the results of western blot analysis in the case of SDS-PAGE under nonreducing condition. HGF-NG precursor protein having a natural α chain-β chain boundary sequence was detected as a single band in the cases not only before but also after activation treatment with FCS (Lanes 1 and 3 in FIG. 2). This means that the active HGF-NG structure was held with S—S bond. The HGF-NG was not activated by Genenase I and did not undergo any other cleavage. Therefore, it remained as a single band (Lane 2 in FIG. 2). Also, in each case of HGF-G1 precursor protein, HGF-G2 precursor protein, and HGF-G3 precursor protein to which a Genenase I recognition sequence was inserted, not only before (Lanes 4, 6 and 8 in FIG. 2) but also after (Lanes 5, 7 and 9 in FIG. 2) Genenase I treatment, only a single band was detected. These facts showed that the HGF precursor protein variants were held with S—S bond even after being cleaved by Genenase I.

Example 2

The active HGF-G1 or active HGF-G3 prepared in Example 1 was subjected to SDS-PAGE under reducing condition, and transferred onto PVDF membrane. The protein transferred onto the PVDF membrane was stained with Coomassie Brilliant Blue, and the 30 kDa band corresponding to the HGF β chain was cut out. The sequence of the N-terminal amino acid was analyzed using an amino-acid sequencer (Procise 491 cLC made by Applied Biosystems). The N-terminal amino acid sequences of the bands thought to be the β chains of HGF-G1 and HGF-G3 were both VVNGI (Val-Val-Asn-Gly-Ile). This confirmed that the HGF precursor protein variant to which a Genenase I recognition sequence was inserted was cleaved at the site of the Genenase I recognition sequence as designed.

TABLE 2

| | Amino-acid sequence | Sequence listing |
|---|---|---|
| HGF | . . . CAKTKQLR↓VVNGI . . . | SEQ ID NO: 14; 482 . . . 494 |
| HGF-G1 | . . . CAKTKQHY↓VVNGI . . . | SEQ ID NO: 19; 482 . . . 494 |
| HGF-G3 | . . . CAPGAAHY↓VVNGI . . . | SEQ ID NO: 20; 482 . . . 494 |
| HGF β chain | VVNGI . . . | SEQ ID NO: 14; 490 . . . 494 |
| HGF-G1 β chain | VVNGI . . . | SEQ ID NO: 19; 490 . . . 494 |
| HGF-G3 β chain | VVNGI . . . | SEQ ID NO: 20; 490 . . . 494 |

Example 3

Figure 3:
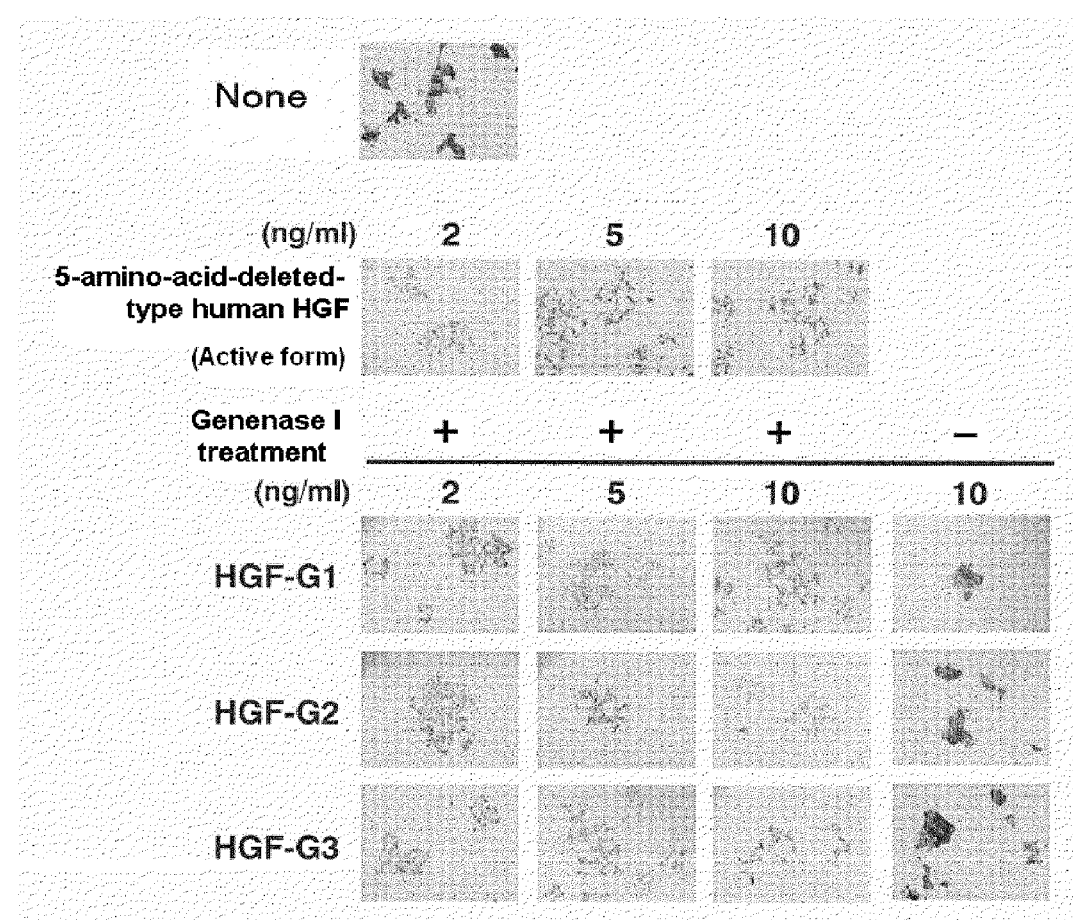
FIG. 3 shows the evaluation results of the scattering action of the sample on the MDCK cells. The samples were obtained by subjecting HGF-G1 precursor protein, HGF-G2 precursor protein and HGF-G3 precursor protein to Genenase I treatment (+).

Canine kidney epithelial cells (MDCK) (Montesano R, et al., Cell, 66, 697-711 (1991))] were suspended in DMEM (containing 10% by volume of FCS) and plated into each well of a 24-well plate at 1×10⁴ cells/well (480 μL/well). A test sample in an amount of 20 μL containing active 5-amino-acid-deleted-type human HGF, the active HGF-G1, active HGF-G2 or active HGF-G3 prepared in Example 1, was added thereto. After incubation at 37° C. for 20 hours, the presence or absence of scattering was observed with a microscope (FIG. 3). The test sample was prepared so as that the concentration of 5-amino-acid-deleted-type human HGF, active HGF-G1, active HGF-G2 or active HGF-G3 was 2, 5 or 10 ng/mL after 20 μL of the test sample was added to the medium.

None of HGF-G1 precursor protein, HGF-G2 precursor protein and HGF-G3 precursor protein to which a Genenase I recognition sequence was inserted showed cell migration action before Genenase I treatment (FIG. 3; −). After Genenase I treatment (FIG. 3; +), all of active HGF-G1, active HGF-G2 precursor protein and HGF-G3 showed cell migration action equivalent to active 5-amino-acid-deleted-type human HGF. This confirmed that the HGF precursor protein variant to which a Genenase I recognition sequence was inserted was converted into a double-stranded chain structure by Genenase I, and therefore, became an active HGF precursor protein variant having HGF action.

INDUSTRIAL APPLICABILITY

The active HGF protein variant of the present invention can be used as an alternative medicament of HGF because it has substantially the same action as HGF.

DRAWINGS

1. Under reducing condition
2. FCS addition または FCS (+)
3. Under nonreducing condition
4. 5-amino-acid-deleted-type human HGF
5. Active form
6. Genenase I treatment

---

The invention claimed is:

1. A hepatocyte growth factor (HGF) precursor protein variant having an α-chain and a β-chain, in which amino acids in the HGF precursor protein variant are substituted with at least one protease recognition sequence, wherein the protein obtained by cleavage at said at least one protease recognition sequence results in a protein having hepatocyte proliferation activity; and wherein said substitution is selected from the group consisting of:
   a) the last four amino acids of the α-chain or the first four amino acids of the β-chain are substituted with Asp-Asp-Asp-Lys (SEQ ID NO: 3), Ile-Glu-Gly-Arg (SEQ ID NO: 4), Ile-Asp-Gly-Arg (SEQ ID NO: 5), Arg-Xaa-Lys-Arg (SEQ ID NO: 10), or Arg-Xaa-Arg-Arg (SEQ ID NO: 11), where Xaa represents any amino acid residue;
   b) the last six amino acids of the α-chain or the first six amino acids of the β-chain are substituted with Leu-Val-Pro-Arg-Gly-Ser (SEQ ID NO: 6), Pro-Gly-Ala-Ala-His-Tyr (SEQ ID NO: 12), or Pro-Gly-Ala-Ala-Tyr-His (SEQ ID NO: 13);
   c) the last seven amino acids of the α-chain or the first seven amino acids of the β-chain are substituted with Glu-Xaa-Xaa-Tyr-Phe-Gln-Ser (SEQ ID NO: 7) or Glu-Xaa-Xaa-Tyr-Phe-Gln-Gly (SEQ ID NO: 8), where Xaa represents any amino acid residue;
   d) the last eight amino acids of the α-chain or the first eight amino acids of the β-chain are substituted with Leu-Glu-Val-Leu-Phe-Gln-Gly-Pro (SEQ ID NO: 9); and
   e) the last two amino acids of the α-chain or the first two amino acids of the β-chain are substituted with His-Tyr or Tyr-His.

2. The HGF precursor protein variant according to claim 1, wherein the HGF is of human, canine or feline origin.

3. The HGF precursor protein variant according to claim 1, wherein the HGF is of human origin.

4. The HGF precursor protein variant according to claim 3, wherein the HGF amino acid sequence into which said protease recognition sequence is substituted is selected from SEQ ID NO: 1 or SEQ ID NO: 2.

5. The HGF precursor protein variant according to claim 3, wherein the HGF amino acid sequence into which said protease recognition sequence is substituted has an α-chain represented by amino acids 32-494 of SEQ ID NO: 1 and a β-chain represented by amino acids 495-728 of SEQ ID NO: 1 or has an α-chain represented by amino acids 32-489 of SEQ ID NO: 2 and a β-chain represented by amino acids 490-723 of SEQ ID NO: 2.

6. An active HGF protein variant wherein the HGF precursor protein variant of claim 1 has been cleaved at one of said protease recognition sequences.

7. The active HGF protein variant according to claim 6, wherein the protease recognition sequence substituted is SEQ ID NO: 3 and the cleavage is caused by Enterokinase protease treatment.

8. The active HGF protein variant according to claim 6, wherein the protease recognition sequence substituted is either SEQ ID NO: 4 or SEQ ID NO: 5 and the cleavage is caused by blood coagulation factor Xa protease treatment.

9. The active HGF protein variant according to claim 6, wherein the protease recognition sequence substituted is SEQ ID NO: 6 and the cleavage is caused by thrombin protease treatment.

10. The active HGF protein variant according to claim 6, wherein the protease recognition sequence substituted is either SEQ ID NO: 7 or SEQ ID NO: 8 and the cleavage is caused by Tobacco Etch Virus (TEV) protease treatment.

11. The active HGF protein variant according to claim 6, wherein the protease recognition sequence substituted is SEQ ID NO: 9 and the cleavage is caused by Rhinovirus 3C protease treatment.

12. The active HGF protein variant according to claim 6, wherein the protease recognition sequence substituted is either SEQ ID NO: 10 or SEQ ID NO: 11 and the cleavage is caused by Furin protease treatment.

13. The active HGF protein variant according to claim 6, wherein the protease recognition sequence substituted is either SEQ ID NO: 12 or SEQ ID NO: 13 and the cleavage is caused by Genenase I protease treatment.

14. The active HGF protein variant according to claim 6, wherein the protease recognition sequence substituted is either His-Tyr or Tyr-His and the cleavage is caused by Genenase I protease treatment.

15. A medicament comprising the active HGF protein variant according to any one of claims 7-14 in combination with a carrier or pharmaceutically acceptable excipient.

16. A method for producing an active HGF protein variant according to any one of claims 7-14 wherein DNA encoding the HGF precursor protein variant is introduced into an isolated host cell, the HGF precursor protein variant is expressed, and the HGF precursor protein variant is cleaved by the protease.

17. A method for producing an active HGF protein variant according to any one of claims 7-14 wherein DNA encoding the HGF precursor protein variant and DNA encoding the protease are simultaneously introduced into an isolated host cell, the HGF precursor protein variant and protease are simultaneously expressed, and the HGF precursor protein variant is cleaved by the protease.

* * * * *